United States Patent [19]

Perkins

[11] Patent Number: 4,705,034

[45] Date of Patent: Nov. 10, 1987

[54] METHOD AND MEANS FOR DISPENSING RESPIRATING GASES BY EFFECTING A KNOWN DISPLACEMENT

[76] Inventor: Warren E. Perkins, 9960 S. A-1-A, Apt. #1901, Jensen Beach, Fla. 33457.

[21] Appl. No.: 783,121

[22] Filed: Oct. 2, 1985

[51] Int. Cl.[4] .................. A61M 15/00; G01F 11/06
[52] U.S. Cl. ........................ 128/204.21; 128/204.26; 222/250
[58] Field of Search ................ 222/249, 250; 128/204.21, 204.26, 205.18

[56] References Cited

U.S. PATENT DOCUMENTS

| 2,755,966 | 7/1956 | Lindars | 222/250 |
| 2,881,959 | 4/1959 | Sheen | 222/250 |
| 3,208,644 | 9/1965 | Bergson | 222/249 |
| 3,235,136 | 2/1966 | Fullman | 222/250 |
| 3,292,824 | 12/1966 | Arp et al. | 222/250 |
| 3,910,270 | 10/1975 | Stewart | 128/204.24 |
| 4,036,221 | 7/1977 | Hillsman et al. | 128/204.23 |
| 4,054,133 | 10/1977 | Myers | 128/142.2 |
| 4,215,409 | 7/1980 | Strowe | 128/204.22 X |
| 4,278,110 | 7/1981 | Price et al. | 128/204.26 |
| 4,279,360 | 7/1981 | Hauser | 222/250 X |
| 4,340,044 | 7/1982 | Levy et al. | 128/204.21 |
| 4,381,002 | 4/1983 | Mon | 128/204.24 |
| 4,457,303 | 7/1984 | Durkan | 128/204.24 |
| 4,519,387 | 5/1985 | Durkan et al. | 128/204.26 |
| 4,542,740 | 9/1985 | Kleinschmidt et al. | 128/204.21 |

Primary Examiner—William E. Wayner
Attorney, Agent, or Firm—Roland H. Shubert

[57] ABSTRACT

A device for administering oxygen and other respirating gases to a patient premeters and temporarily stores single dose quantities of respirating gas and dispenses each dose in synchronization with the patients's inspiratory cycle. A sensor produces a signal upon the onset of each inhalation and a single dose of gas is dispensed to the patient in immediate response to the sensor signal.

12 Claims, 13 Drawing Figures

METHOD AND MEANS FOR DISPENSING RESPIRATING GASES BY EFFECTING A KNOWN DISPLACEMENT

BACKGROUND OF THE INVENTION

This invention relates generally to methods and apparatus for administering oxygen and other respirating gases to a patient.

More particularly, this invention relates to methods and means for administering oxygen and other gases to a patient on an intermittent, respiration controlled, basis.

It has become common medical practice to treat patients suffering from advanced stages of chronic obstructive pulmonary diseases by administration of oxygen. Such pulmonary diseases, including chronic bronchitis, emphysema and severe asthma, are one of the fastest rising causes of death in the United States affecting probably more than ten million people. It is estimated that more than 500,000 people in the United States either are routinely receiving oxygen therapy or could benefit from it. Much of this rather expensive treatment is funded by Medicare.

The devices which commonly have been used to deliver oxygen to a patient meter the oxygen flow at a fixed rate and deliver a constant stream of oxygen to the patient. Oxygen is received by the patient either through a mask which is placed over the nose and mouth or through a cannula which terminates in nares inserted into the patient's nostrils.

It has long been recognized that providing a constant flow of oxygen to a patient results in the waste of a substantial proportion of the oxygen supply. The normal breathing cycle consists of an inhalation, an exhalation longer in duration than the inhalation, and then a pause before the next cycle oxygen supplied to a patient during the exhalation and pause phases of the respiratory cycle is totally wasted. Devices have been developed to conserve oxygen by regulating the oxygen flow, turning it on and off, in response to the respiratory cycle. Typical of such devices are those of Myers, U.S. Pat. No. 4,054,133, and Mon, U.S. Pat. No. 4,381,002. Each of these patents disclose devices which sense inhalation and exhalation pressures in the nasal cavity of a patient and converts those sensed pressure differentials to signals which control the flow of oxygen to a patient. Typically, oxygen flow is started upon the sensing of a negative pressure relative to atmospheric indicating the start of an inspiration period. Oxygen flow is then stopped at a second signal produced by the sensing of a positive pressure relative to atmospheric indicating the start of the expiration period.

More recently, Dr. Gerald Durkan clinically observed that only the oxygen supplied during the initial part of an inspiration period was efficiently absorbed by a patient. It is that first inspired portion of oxygen which reaches the alveoli while oxygen supplied during the latter part of an inspiration period remains in nonabsorbing areas such as the pharynx, trachea and bronchial tubes. Durkin concluded that supplying oxygen at a high rate, beginning at the start of inspiration but lasting only for a small portion of the inspiration period offered economic and physiologic advantages over those prior techniques which supplied oxygen during the entire inspiration period.

As a result of his observations, Durkan developed a respirator system known as the Demand Oxygen Controller which is disclosed in U.S. Pat. No. 4,457,303. That respirator system uses a fluidic laminar proportional amplifier to sense the start of an inspiration period. Oxygen flow to a patient is immediately started in response to the sensed inspiration. Timing means, also started in response to the sensed inspiration, stop the oxygen flow after a preset period of time which is shorter than is the inspiration period. As a result, oxygen is supplied to a patient only during the effective, early stages of an inspiration resulting in an oxygen savings of as much as 70% as compared to a continuous flow administration.

All of these prior art techniques have one property in common. All determine or control the volume of oxygen (or other respirating gas) delivered to the patient over a respiratory cycle by controlling both the rate at which oxygen is allowed to flow and the time or duration of oxygen flow for each respiratory cycle. Both Myers and Mon teach the starting of oxygen flow upon sensing the beginning of an inspiration and the stopping of oxygen flow upon the sensing of an expiration. Durkin teaches the starting of oxygen flow upon sensing the beginning of an inspiration and stops oxygen flow at the end of a time period which is independent from, and shorter than, the inspiration period.

Those prior art devices which connect a rate metered supply of oxygen to a cannula for a predetermined time to effect the desired dose delivery all have the disadvantage that both the rate and duration of flow must be precisely controlled if the dose is to be accurately measured and dispensed. Because of the small quantities of oxygen required per dose (typically about 33 cc measured at standard temperature and pressure), it is difficult and expensive on a production basis to provide for the degree of accuracy of flow rate and of timing required to ensure a safe dose efficiently delivered for each breath. An improved and simplified way to dispense an oxygen dose in synchronization with a patient's respiratory cycle provides clear advantages in this art.

SUMMARY OF THE INVENTION

A method and apparatus for administering oxygen or other medical gases to a patient in sychronization with the respiratory cycle of the patient operates by generating a signal in response to the onset of an inhalation and immediately dispenses a premeasured volume of the oxygen or other gas by effecting a known displacement. Displacing means suitable for use include a cylinder containing a spring loaded piston which is filled from a pressurized gas supply forcing the piston back to a stop set to control the volume. Other displacing means include a double acting piston within a cylinder and a pressurized, adjustable volume which is blown down into the cannula for dose delivery. In another embodiment, there is provided means to simultaneously deliver two gases, for example oxygen and nitrous oxide, by using two coupled displacers.

Hence, it is an object of this invention to provide a method and means to supply measured doses of respirating gases to a patient during the early stages of each inspiration and dispensing a premeasured gas volume by effecting a known displacement.

It is another object of this invention to provide a simplified respirator apparatus which does not employ timing means to control dose volume.

Yet another object of this invention is to provide a method and means for simultaneously dispensing two different gases in while controlling the volume of gases dispensed and the ratio of one gas to the other in a simple, fail-safe manner.

Other objects of this invention will be apparent from the following description of certain embodiments of the invention.

DESCRIPTION OF THE DRAWING

Specific embodiments of the invention are illustrated in the drawing in which:

FIG. 6-A shows another control circuit especially useful with the embodiments of FIGS. 2 and 4;

FIG. 7-A illustrates one means for changing the unit dose of gas delivered by the dispensing means of FIG. 7;

FIG. 7-B illustrates a second means for changing the unit dose of gas delivered by the dispensing means of FIG. 7;

FIG. 7-C illustrates another embodiment of FIG. 7 wherein a diaphragm means is used in place of a double-acting piston;

DESCRIPTION AND DISCUSSION OF THE INVENTION

Figure 1:
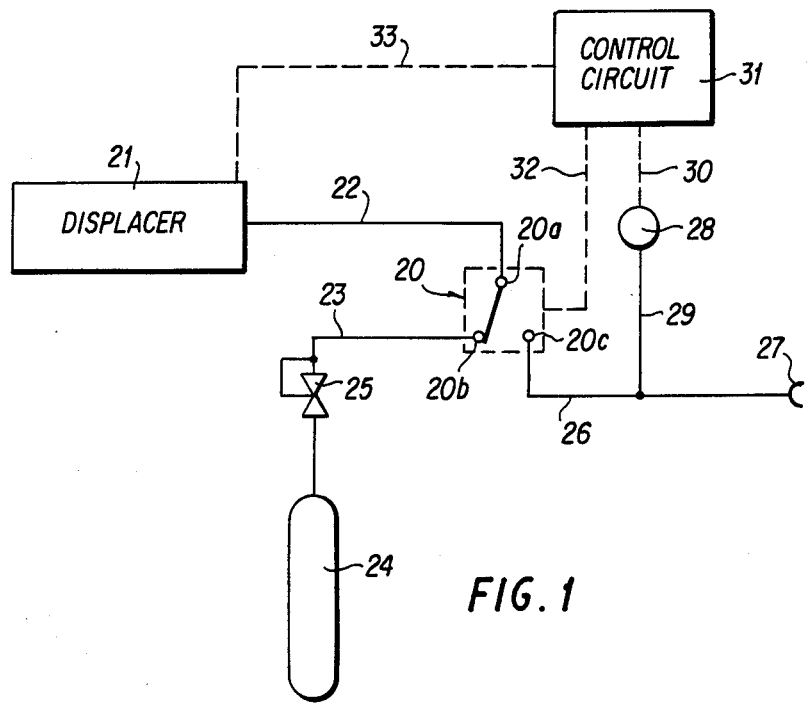
FIG. 1 is a schematic diagram showing generally the gas supply apparatus of this invention.

Various embodiments of this invention will be described and discussed in detail with reference to the drawing figures in which like reference numerals refer to the same component or part illustrated in different figures.

Referring first to FIG. 1, there is shown in its simplist schematic form the gas supply apparatus of this invention. The device comprises a three-way valve means 20 having its common port 20a connected to a displacer means 21 by way of a conduit 22. One of the two option ports 20b is connected by line 23 to a supply of respirating gas, typically oxygen, 24. Gas delivered through line 23 is maintained at a relatively constant pressure, typically about 20 psig, by means of pressure regulator 25. The other option port, 20c, is connected to a cannula or other delivery system 26 which terminates in nares or mask 27.

In use, with valve 20 in the position shown, oxygen from source 24 at the pressure controlled by regulator 25 flows directly to displacer 21. There it effects a preset displacement equal to a unit dose, for one breath, of oxygen measured at standard conditions. Displacer 21 thus performs two distinct functions. First, it premeters or measures a quantity or mass of gas equal to the prescribed unit dose for one breath. Second, it temporarily parks or stores that premetered quantity, or unit dose and then releases that stored unit dose in synchronization with the onset or start of the patient's inhalation. By first premetering and then temporarily storing each single or unit dose of gas, the source of respirating gas is always isolated from direct communication with the patient by the displacer which provides significant safety features not attainable with conventional devices.

Displacer 21 may be of two distinct types, each type operating in a different mode but accomplishing esentially the same result. In one type of displacer, gas is mechanically pushed, or displaced from, a known volume through action of a piston, diaphram or similar means. In a second type of displacer which is advantageous to use at high source pressures, there is provided a fixed volume reservoir which is filled or loaded at source pressure and which discharges a unit dose to the patient by releasing, or blowing down, the pressurized gas within the reservoir to essentially atmospheric pressure.

It is conventional to express a unit dose of respirating gas in terms of a gas volume at standard temperature and pressure. Gas dispensing means of this general type typically operate at ordinary room temperature so gas volume changes due to temperature variations may be safely ignored. Hence, the operating volume of both types of displacer 21 is dependent upon the pressure of the gas source. For example, if the volume of oxygen prescribed for one breath or unit dose is 33 cc (approximately equal to a continuous rate of 2 liters per minute), then the required displacement volume the first described type of displacer at a source pressure of 20 psig would be about 14cc. Were the second type of described displacer (the embodiment of FIG. 4) to be used, then at a source pressure of 20 psig, the reservoir volume required would be about 24 cc. In either type of displacer, a change in the prescribed unit dose of respirating gas is accommodated by changing the displaced volume (or blowdown volume) in ways which will later be described. It is, of course, also possible to control, or change, the unit dose by changing the source pressure but that dose size control method is less preferred.

Each dose of oxygen must be delivered in synchronization with the patient's inspiratory cycle. To accomplish that synchronous delivery necessarily requires an extremely sensitive and fast responding sensor 28 which is operably connected to cannula 26 by means of line 29 so that, for example, it may monitor and respond to slight changes of pressure occurring in the nasal cavity of the patient. Exemplary sensors meeting those requirements and known in the prior art include a spring-loaded diaphragm sensor as shown by Myers in U.S. Pat. No. 4,054,133 and fluidic devices employing laminar proportional amplifiers as shown by Mon in U.S. Pat. No. 4,381,002 and Durkin in U.S. Pat. No. 4,457,303. A thermistor-type sensor responsive to directional gas flow may also find use in the devices of this invention. Also, a sensitive pressure-to-electric switch, such as the Microswitch, Series 160, may be employed.

Sensor 28 is arranged to produce a signal upon detection of the beginning of an inhalation by the patient. The signal, which may be electrical or pneumatic, is transmitted via means 30 to control circuit 31. Control circuit 31, responding to the signal from sensor 28, activates triggering means 32 causing valve 20 to move to its other position connecting port 20a with port 20c. In this position, oxygen source 24 is isolated from the remainder of the system and the unit dose of oxygen in displacer 21 surges through line 22 and valve 20 into cannula 26 and thence to the patient. A signal 33 is produced by displacer 21 upon completion of the delivery of a unit dose of oxygen causing control circuit 31 to reset valve 20 to its original position thus beginning the cycle anew.

Figure 2:
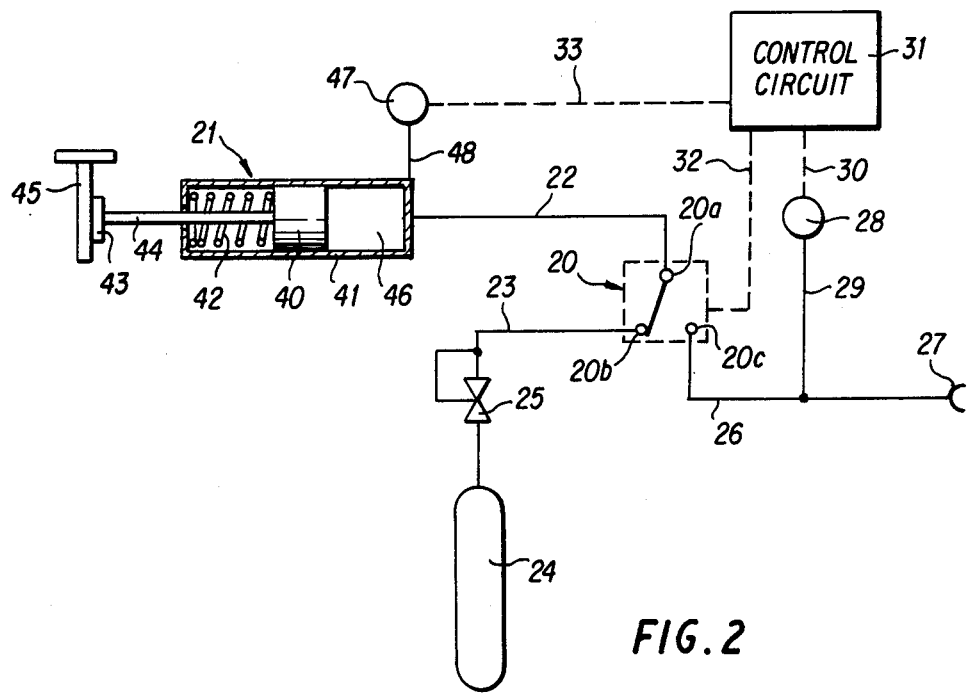
FIG. 2 illustrates in partial section one embodiment of a displacement dispenser for use with the gas supply apparatus.

FIG. 2 illustrates the gas supply apparatus of FIG. 1 which utilizes a piston-type displacer 21. In this embodiment, displacer 21 comprises a piston 40 operating within a cylinder 41. When valve 20 is in the position illustrated, with port 20a connected to port 20b, oxygen from source 24 enters the end of cylinder 41 through line 22 forcing piston 40 back against spring 42 until the end 43 of piston rod 44 engages stop 45. Stop 45, in a preferred embodiment, is adjustable so as to allow varying the volume 46 (and hence the unit dose of oxygen administered per breath) within cylinder 41 when the piston 40 is at the limit of its travel.

So long as valve 20 is in the position shown, pressure exerted upon the head of piston 40 by the gas from source 24 maintains spring 42 under compression and the piston rod end 43 firmly against stop 45. Upon detection of the start of an inhalation by the patient, sensor 28 transmits a signal via 30 to control circuit 31 which in turn causes valve 20 to move to its other position with valve port 20a connected to port 20c. Spring 42 then forces the piston 40 forward to the end of cylinder 41 causing the gas within the cylinder to surge through line 22 and valve 20 into cannula 26 and thence to the patient. A position sensor 47, which may comprise a differential pressure switch, a magnetic reed switch or a microswitch, is operably arranged through means 48 to detect the completion of the piston travel and to transmit a signal 33 to control circuit 31. Thereupon, valve 20 resets to its refill position and the fixed volume 46 is refilled for the next cycle.

Figure 3:
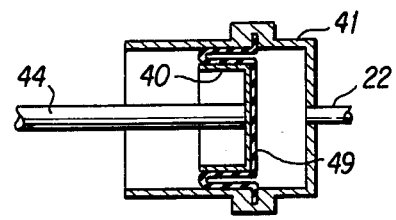
FIG. 3 illustrates a rolling diaphragm type of piston displacing means preferred in certain embodiments of this invention.

One particularly preferred piston and cylinder arrangement for use as the displaces 21 of this invention is illustrated in FIG. 3. This device is commercially available under the tradename Bellofram Rolling Diaphram and is described in detail in U.S. Pat. Nos. 3,137,215 and 3,373,236. As shown in FIG. 3, the device includes a diaphragm 49 which is formed in the shape of a truncated cone with its center fastened to the head of piston 40 and its outer flange clamped to cylinder 41. Diaphragm 49 alternately rolls and unrolls on the skirt of piston 40 and the wall of cylinder 41 as the piston travels back and forth. The rolling action of diaphragm 49 eliminates sliding contact and breakaway friction. The diaphragm arrangement forms a complete seal preventing blow-by leakage and pressure loss and requires no lubrication of any kind. These features make the device highly advantageous to use in the dispensing of respirating gases to a patient.

Figure 4:
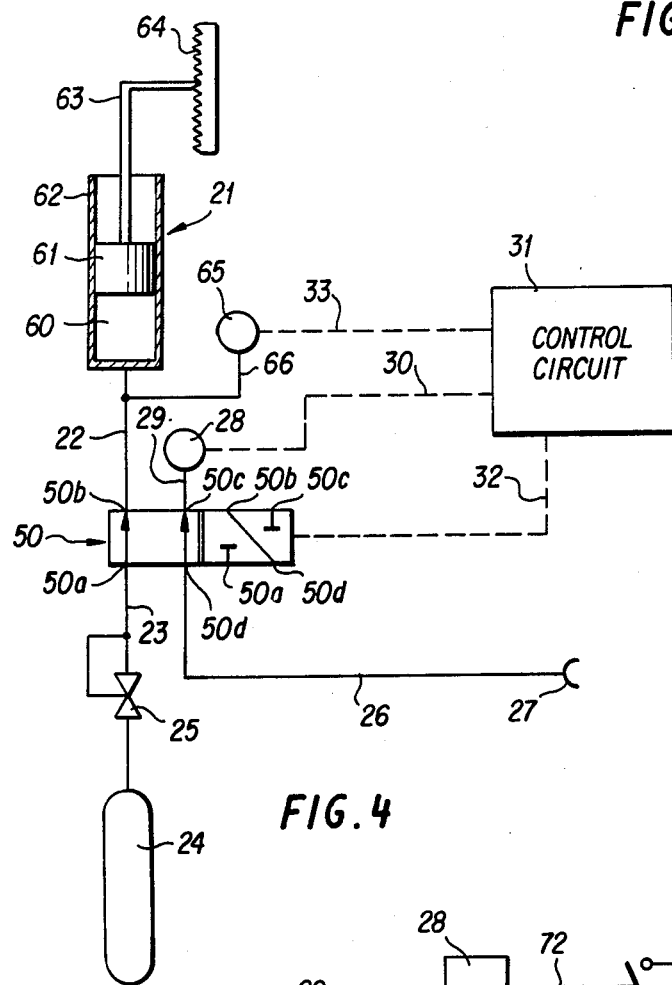
FIG. 4 is a diagram in partial section of a fixed volume, but adjustable, gas dispensing means.

FIG. 4 illustrates another embodiment of this invention which is especially useful with higher pressure oxygen sources such as those central systems having distribution lines to multiple locations as in many hospitals and other health care facilities. Those central systems typically maintain an oxygen pressure of about 50 psig in the distribution lines. This embodiment employs a two-position valve 50 having four ports 50a, 50b, 50c and 50d. In the valve position shown, the gas source 24 is connected through valve ports 50a and 50b and line 22 directly to a fixed volume chamber 60 within displacer 21. The displacer unit in this embodiment may comprise a piston with a rolling diaphragm as is illustrated in FIG. 3. Unlike the embodiment of FIG. 2, however, piston 61 within cylinder 62 remains stationary during operation of the gas supply apparatus. Provision is made for changing, or setting, the volume 60 (in order to fix a unit dose of oxygen dispensed per breath) by moving piston 61 up and down through connecting rod 63 which is adapted to lock into adjustment rack 64 at the desired volume or unit dose position.

While valve 50 is in the first, or fill, position sensor 28 is connected via line 29 and valve ports 50c and 50d to the cannula 26. Upon the detection of the start of an inhalation, sensor 28 produces a signal which is transmitted to control circuit 31 by means 30. That signal may be either pneumatic or electrical depending upon the type of device employed as the sensor 28. The signal from sensor 28 causes control circuit 31 to actuate valve 50 through means 32 and so change the valve to its other position. In this other position, valve port 50b is connected to port 50d while ports 50a and 50c are isolated from the system. Pressurized gas in fixed volume chamber 60 thus has an open flow path via line 22, through valve 50 to cannula 26 and thence to the patient causing the pressure within chamber 60 to drop rapidly to essentially atmospheric. A differential pressure switch, or other suitable sensor, 65 is connected to chamber 60 through conduit 66 and transmits a signal via means 33 to the control circuit 31 upon depletion of the pressure within chamber 60. The signal causes the control circuit 31 to reset valve 50 back to its original, or refill, position thus starting a new cycle The valving arrangement depicted in this embodiment isolates sensor 28 from the pressure surge which occurs as oxygen flows from chamber 60 to the patient. This arrangement is advantageous in those cases wherein the construction of sensor 28 might be damaged by sudden positive over pressures. This valving arrangement may, of course, also be used in the embodiment depicted in FIG. 2. In addition to simplicity, the compact size of the device of this embodiment may be appreciated by calculation of the volume 60 required to deliver a unit dose of 33 cc of oxygen measured at standard conditions. At a system pressure of 50 psig, volume 60 would be set at approximately 10 cc to deliver 33 cc of oxygen measured at atmospheric pressure.

Figure 5:
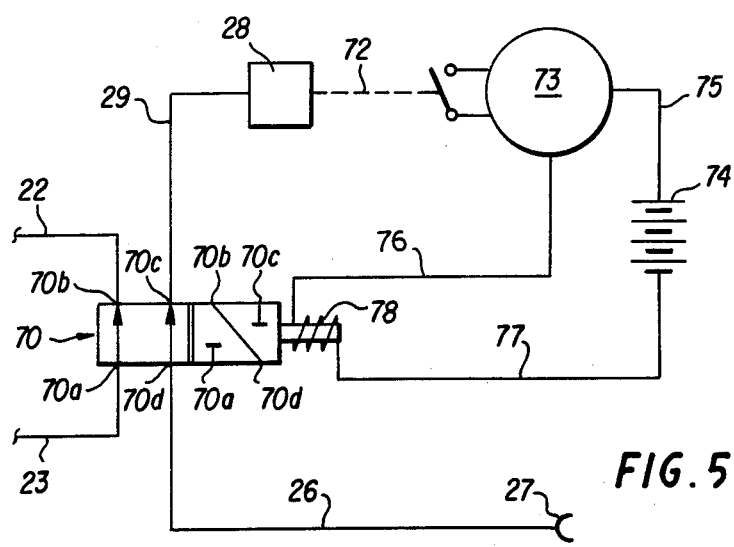
FIG. 5 schematically depicts one specific control circuit preferred for use with certain embodiments of this invention.

Control circuit 31 has been described in functional terms in relation to the embodiments shown in FIGS. 1, 2 and 4. FIG. 5 illustrates details of a control circuit especially adapted to the embodiment of FIG. 4 but also appropriate for use with the embodiment of FIG. 2. There is shown a four-way, two position valve 70 in the refill position wherein line 23 communicates with a source of respirating gas via port 70a and line 22 leads to a displacer via port 70b. Cannula 26 is connected to line 29 and sensor 28 through ports 70c and 70d. Sensor 28 may be of any type having adequate sensitivity to detect the onset of inhalation. It may, for example, be a very sensitive pressure switch, a fluidic amplifier or a thermistor which reacts to flow. Sensor 28, upon detection of the onset of an inhalation, produces a trigger signal 72 which activates interval timer 73. Interval timer 73 is of the type commonly called a one-shot timer or a time delay relay which, upon receiving the trigger signal, initiates a timed cycle of power from power supply 74.

This cycle of power, traveling through conductors 75, 76 and 77, activates the solenoid coil 78 of valve 70 causing it to move to its other position wherein port 70b is connected to port 70d and wherein ports 70a and 70c are isolated from the system. At the end of the cycle period, the electric power pulse stops, valve 70 returns to its original, or reset, position, and the interval timer 73 resets to an "off" position until the next trigger signal. The exact duration of the electric power pulse produced by interval timer 73 is not important so long as it is long enough to permit complete delivery of the stored pulse volume in the displacer chamber and short enough to allow sufficient time for the metering chamber (volume 60 of FIG. 4) to refill in time for the next cycle. A range of times from about $\frac{3}{8}$ to $\frac{3}{4}$ of a second is generally appropriate with a period of $\frac{1}{2}$ second being a good design target. It is important to note that dose volume is, within wide limits, completely independent of electric pulse duration; the volume of a unit dose being directly determined by effecting a known displacement.

The control circuit of FIG. 5 may also be modified to employ pneumatic means, rather than the illustrated solenoid coil 78, to cause valve 70 to move from one position to the other. In this embodiment, gas stored under pressure in displacer 21 may be used as the motive fluid to power the valve actuator. Gas used to power valve movement need not be wasted but may be discharged into cannula 26 for use by the patient.

Figure 6:
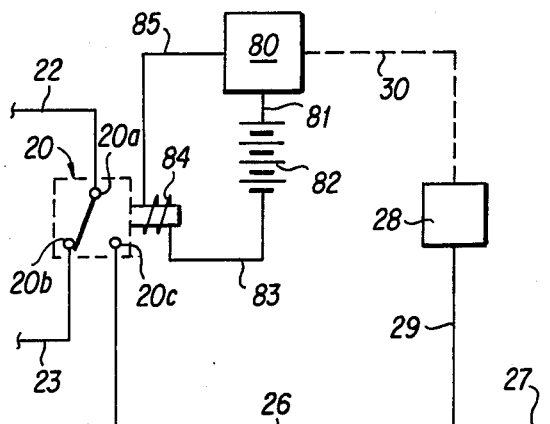
FIG. 6 illustrates another control circuit suitable for other embodiments of this invention.
Figure 6A:
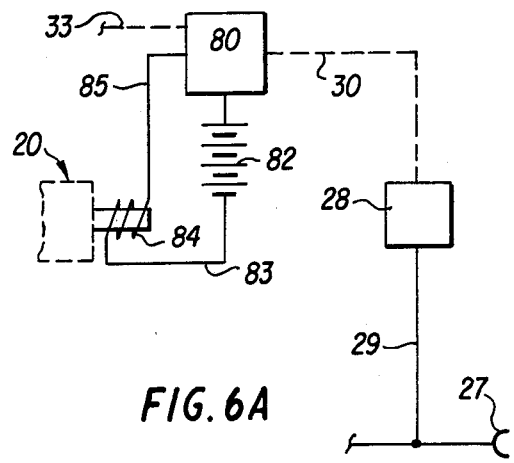

FIG. 6 illustrates another control circuit which is particularly adapted for use with the embodiment of FIG. 2. The circuit includes a flip-flop relay 80 in series connection via conductor 81 with a power supply 82, second conductor 83, valve solenoid coil 84 and third conductor 85. Sensor 28, in this embodiment, detects the onset of both an inhalation and an exhalation and transmits a trigger signal to relay 80 upon the occurrence of each event. As shown in the FIGURE, valve 20 is in the refill position wherein the displacer is in direct communication with a source of respiring gas. Upon receiving a signal representative of the onset of an inhalation from sensor 28, flip-flop relay 80 will, through activation of solenoid coil 84, cause valve 20 to move to its other position. The valve 20 in its other position puts the displacer via line 22 into direct communication with cannula 26. Valve 20 remains in this other position until relay 80 receives from sensor 28 a second signal representative of the onset of an exhalation. At that time, relay 80 causes valve 20 to return to its original, or refill, position. The onset of an inhalation produces a small negative pressure relative to ambient while the onset of an exhalation produces a slight positive pressure relative to ambient. Thus, sensor 28 can be arranged to produce signals of different polarity, corresponding to negative and positive pressures, which ensures that flip-flop relay 80 will cause valve 20 to remain in proper synchronization with the breathing cycle of the patient.

FIG. 6-A shows yet another variation of control circuit 31 which is adaptable for use with the embodiments of both FIGS. 2 and 4. This embodiment uses a flip-flop relay 80, as does the circuit of FIG. 6, but sensor 28 is arranged to produce a signal only upon the onset of an inhalation. Upon receiving a signal from sensor 28, relay 80 activates the solenoid coil 84 of the valve means to that valve position wherein a unit dose of oxygen or other respiring gas is delivered from the displacer to the cannula. A signal 33 is received by relay 80 from the displacer (as was described in relation to FIGS. 2 and 4) when the piston has reached the limit of its travel (FIG. 2) or when the pressure within the fixed volume chamber has depleted to atmospheric (FIG. 4). Signal 33 causes relay 80 (and coil 84) to flip to its other, or refill, position thus completing a cycle.

Figure 7:
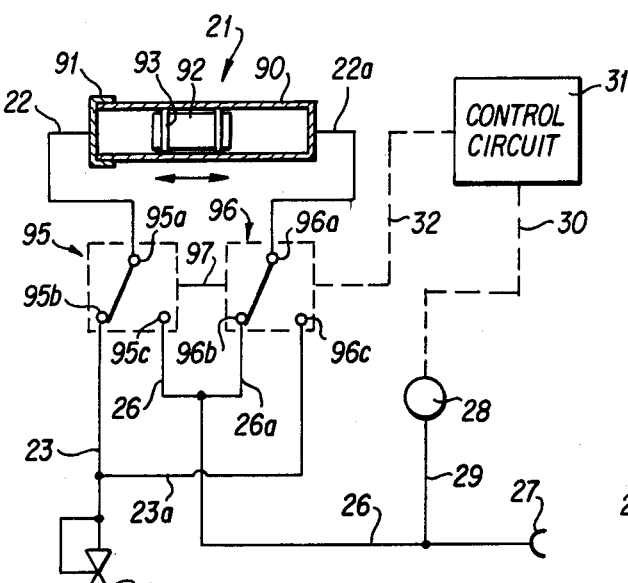
FIG. 7 depicts in partial section another embodiment of the invention which employs a double-acting piston as the gas dispensing means.
Figure 7A:
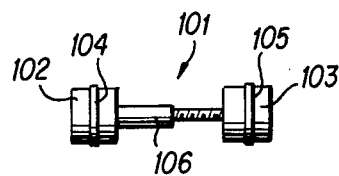
Figure 7B:
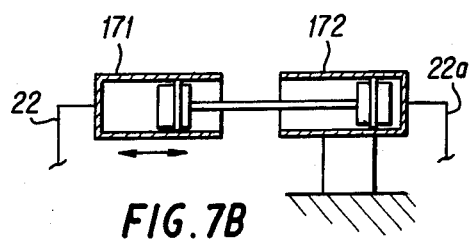
Figure 7C:
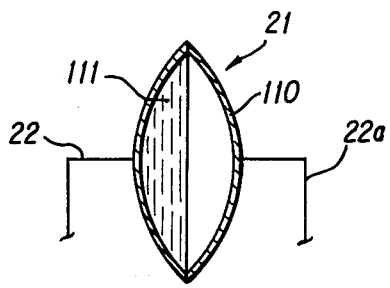

FIG. 7 depicts another embodiment of the gas supply apparatus of this invention which employs a double-acting piston as the gas dispensing means. In this embodiment, displacer 21 comprises a closed cylinder 90, shown in section, and having at least one removable end cover 91. Disposed within cylinder 90 is piston 92 which is free to reciprocate back and forth from one end of cylinder 90 to the other as is shown by the arrows. Piston 92 preferably has sealing rings 93 or other means to minimize gas leakage or blow-by between the piston and cylinder walls. It is short in length as compared to the length of cylinder 90 and preferably is of low weight construction. The piston and cylinder are sized relative to each other so that the free space, or volume, within the cylinder with the piston present is equal to the unit dose of oxygen or other respirating gas which it is desired to administer to a patient at each breath. The size of a unit dose may be changed by removing end cap 91 from cylinder 90 and replacing piston 92 with a similar piston but of either shorter or longer length. This has the advantage of preventing the patient from changing the prescription without the physician's knowledge.

As is shown in the drawing, there is provided two, three-way, two position valves, 95 and 96, ganged together by connecting means 97. Valve 95 includes a common port 95a and two option ports 95b and 95c. Likewise, valve 96 includes common port 96a and option ports 96b and 96c. Common port 95a of valve 95 communicates via line 22 with the interior of cylinder 90 at one end thereof while common port 96a of valve 96 communicates via line 22a with the interior of cylinder 90 at the other end thereof. Respirating gas supply line 23 branches upstream of the valves with one branch 23 communicating with option port 95b of valve 95 and the other branch 23a communicating with option port 96c of valve 96. Cannula 26 also branches downstream of the valves with one branch 26 connecting to option port 95c of valve 95 and the other branch 26a connecting to option port 95b of valve 96. Control circuit 31 is arranged to receive a signal from sensor 28 via transmitting means 30 upon the detection by sensor 28 of the onset of an inhalation. Upon being triggered by a signal received from sensor 28, the control circuit 31 acting through power circuit 32 causes valves 95 and 96 to move from one position to the other position.

Following the operation of the device through one complete respiratory cycle, FIG. 7 shows the source of respirating gas, typically oxygen, connected through valve 95 to the interior of cylinder 90 at the left end thereof. The other end of cylinder 90 is in open communication with the cannula 26 by way of line 22a, valve ports 96a to 96b, and line 26a for the delivery of a dose of oxygen to a patient through nares 27. Because the oxygen supplied through line 23 is at an elevated pressure, typically about 20 psig, it forces piston 92 to the right end of cylinder 90 pushing out the oxygen in that end of the cylinder through line 22a. When the piston reaches the right end of the cylinder 90, it stops and the free space, or cylinder volume, to the left of the piston is filled with oxygen at a pressure equal to the supply pressure. Upon detection by sensor 28 of the onset of the next inhalation, control circuit 31 causes each of valves 95 and 96 to move to its other position whereat port 95a is now connected to port 95c and likewise with valve 96 wherein port 96a is now connected to port 96c. In this second position, oxygen at source pressure is routed to the right end of cylinder 90 by way of line 23a to valve port 96c, out of the valve at port 96a and through line 22a to the interior of cylinder 90. Also, the left end of cylinder 90 is now connected with cannula 26 by way of line 22, valve ports 95a and 95c and line 26 for delivery of an oxygen dose to the patient. Piston 92 is forced to the left end of cylinder 90 by the pressure of oxygen from the supply line and the oxygen pressure within the cylinder 90 at the free space to the right of the piston thereafter reaches equilibrium with the oxygen supply. Upon detection by sensor 28 of the onset of the next inhalation, valves 95 and 96 are caused by control circuit 31 to return to their original position and the cycle begins anew.

It has earlier been noted that the volume of a unit dose dispensed by the device of FIG. 7 can be changed by replacing piston 92 with a similar piston of either greater or shorter length. FIG. 7-A illustrates another approach to changing the unit dose in which there is provided an adjustable length piston 101. Piston 101 comprises two end members, 102 and 103, having sealing rings 104 and 105 respectively. A threaded connecting rod 106 is disposed between the two end members and is arranged so that the distance between end members 102 and 103 may be adjusted thus changing the overall length of piston 101.

A second alternative embodiment of a displacer which may be used in place of cylinder 90 of FIG. 7 is illustrated in FIG. 7-B. In this embodiment, there are provided two open ended, axially aligned, cylinder members 171 and 172 which are shown in section. A pair of pistons 173 and 174, each having a sealing ring 175 and 176 and connected by fixed length piston rod 177, are disposed in cylinder members 171 and 172 respectively. Cylinder members 171 and 172 are movable one relative to the other as by mounting cylinder 172 on support 178 while making provision for limited axial adjustment of cylinder 171. As can readily be appreciated, a change in the position of cylinder 171 relative to cylinder 172 acts to change the volume displaced by movement of the connected pistons thus adjusting or setting a unit dose of respirating gas.

FIG. 7-C illustrates an alternative, but less preferred, embodiment of a displacer which may be used in place of cylinder 90 of FIG. 7. The displacer, shown in section, comprises a symmetrical shell 110 having a flexible membrane 111 disposed across the interior center of the shell to divide it into two compartments. Gas lines 22 and 22a communicate with the interior of shell 110 at opposite sides thereof. In operation, membrane 111 is the functional equivalent of piston 92 within cylinder 90 displacing gas from first one side and then the other of membrane 111.

Figure 8:
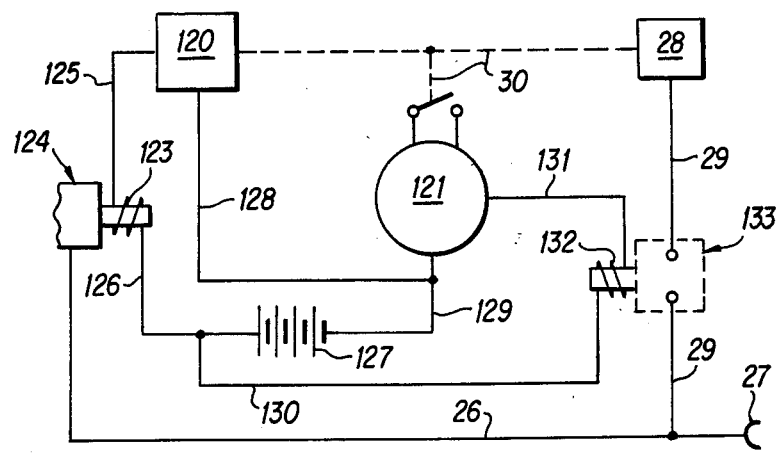
FIG. 8 schematically depicts a control circuit useful in the embodiment of FIG. 7.

Turning now to FIG. 8, there is shown a control circuit which has particular use with the embodiment of this invention illustrated in FIG. 7 but which may also be used with the inventive embodiments of FIGS. 2 and 4. In the circuit shown, sensor 28 is arranged to produce a signal only upon the detection of the onset of an inhalation. That signal 30 is transmitted to a flip-flop relay 120 and is also transmitted to a time delay relay 121. The signal 30 triggers flip-flop relay 120 activating solenoid coil 123 of flow control valve 124 by way of the circuit comprising conductors 125 and 126, power supply 127 and conductor 128. Flow control valve 124 may be a three-way valve as in FIG. 2; a four-way valve as in FIG. 4; or a pair of ganged three-way valves as shown in FIG. 7. Trigger signal 30 also activates internal timer 121 which, upon receiving the trigger signal initiates a timed cycle of power from power supply 127 by way of conductors 129, 130 and 131 causing solenoid coil 132 to change the position of valve 133. Valve 133 is a simple two-way isolating valve which is inserted into line 29 connecting sensor 28 with cannula 26. Valve 133 is arranged to be in the closed position while solenoid coil 132 is activated by interval timer 121. The power pulse produced by interval timer 121 is long enough, typically about ½ second, to shield the sensor 28 from the rush of respirating gas released upon the onset of an inhalation by movement of flow control valve 124. At the end of timed interval, solenoid 132 is de-energized and valve 133 returns to the open position re-connecting sensor 28 with cannula 26.

Figure 9:
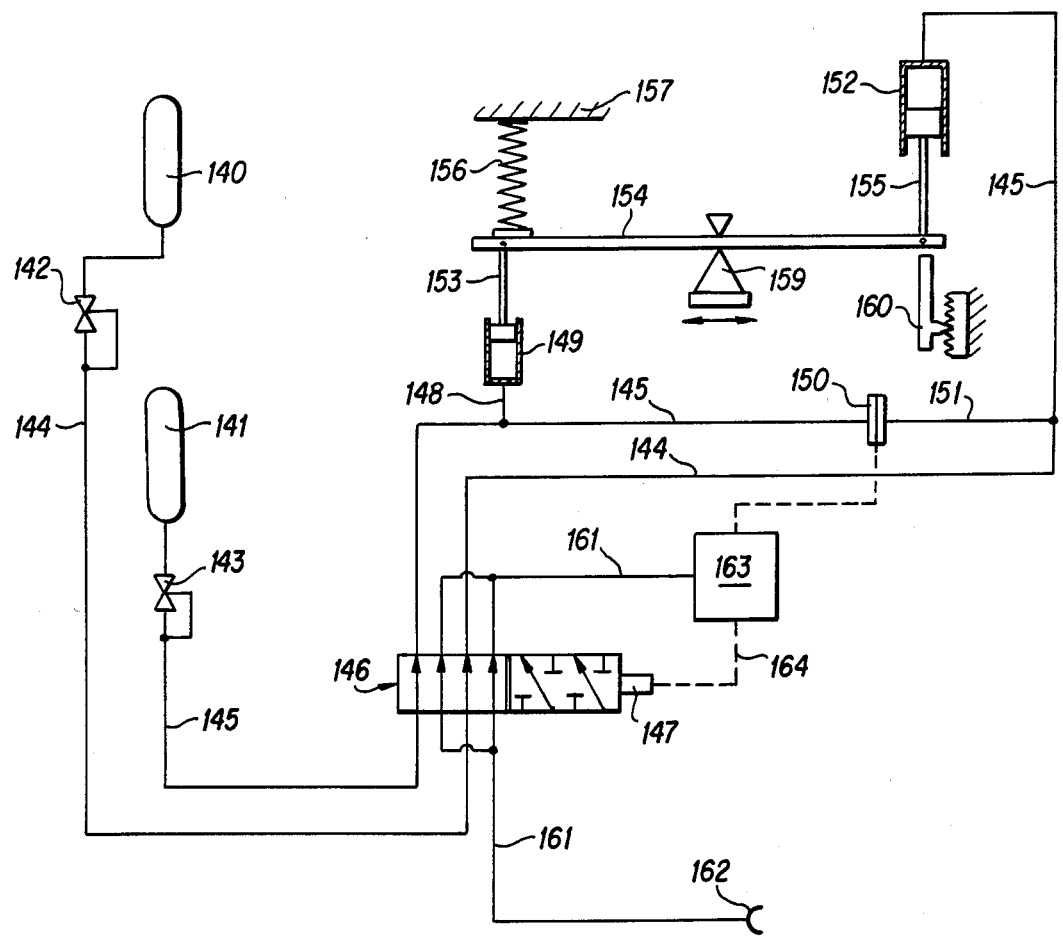
FIG. 9 is a schematic diagram showing an arrangement for simultaneously delivering coordinated doses of two different gases.

Referring now to FIG. 9 there is shown a schematic arrangement for delivering coordinated doses of both oxygen and a second gas having anesthetic or other physiological effects simultaneously in response to an inhalation signal. There is provided sources of oxygen 140 and a second gas 141 which may be, for example, nitrous oxide. Each gas supply is regulated to essentially the same pressure by regulators 142 and 143 and conveyed by way of lines 144 and 145 to a two position, four circuit valve 146. Valve 146 is diagrammed in its normal, or unpowered, position. The right half of the valve diagram indicates the flow pattern through valve 146 in its other position; that is, when it is powered by activator 147 which may be a solenoid coil or a pneumatic activator.

Second, or anesthetic, gas line 145 continues through valve 146, branches at 149 to communicate with the interior of piston-type displacer 149, and terminates at differential pressure switch 150. In similar fashion, oxygen gas line 144 continues through valve 146, branches at 151 to communicate with the other side of differential pressure switch 150, and terminates at a second piston-type displacer 152. It is preferred that displacer 149 and 152 be of the type illustrated in FIG. 3.

Connecting rod 153 of displacer 149 is pivotally attached near one end of coordinating lever 154 while connecting rod 155 of displacer 152 is pivotally attached at a point near the other end, and at the opposite side 01, lever 154. A dose delivery spring 156, fixed at one end to support 157, is arranged so that its other end bears on lever 154 at a point 158 near the lever end. Flow of the two gases, oxygen and the second gas, through valve 146 and to their respective displacers, 152 and 149, forces the pistons to act on the coordinating lever 154 making it pivot at pivot point 159 and compress dose delivery spring 156. Spring 156 is selected to have a spring rate which is not quite strong enough to resist the force of the compressed gases within the two displacers. Movement of the lever 154, and accordingly the piston travel in displacers 149 and 152, is limited by dose size adjustment stop 160 located at the other end and the opposite side of lever 154 from the dose delivery spring 156. The dose size adjustment stop 160 controls the length of piston travel of displacer 152 thereby allowing selection of the desired oxygen dose volume. Pivot point 159 is preferably adjustable along the length of coordinating lever 154. Movement of the pivot point 159 changes the ratio of piston travel of one displacer to the other thereby changing the ratio of oxygen (delivered by displacer 152) to anesthetic gas (delivered by displacer 149). The relative cross sections of displacers 149 and 152 are, of course, also a factor in establishing the basic gas ratio.

There is provided a cannula means 161 terminating in nares 162 to deliver doses of oxygen mixed with anesthetic gas to the patient. Cannula 161 splits into two branches just before valve 146 which provides communication through two of the four circuits of valve 146 while the valve is in its normal position. The two branches of cannula 161 rejoin on the other side of valve 146 and lead into control means 163. Control means 163 comprises a circuit of the type described in FIG. 5 including a sensor adapted to produce a trigger signal at the onset of an inhalation. Upon receiving a triggering signal representative of the beginning of an inhalation, control means 163 acting through means 164 triggers activator 147 causing valve 146 to move to its other position which is diagrammed on the right half of the valve. In this second position, gas supply lines 144 and 145 from the gas sources are terminated at valve 146. The extensions of these two lines on the other side of the valve and leading to the two displacers 149 and 152 are shunted into cannula 161. The force of dose delivery spring 156 on the end of coordinating lever 154 rapidly empties the two displacers thus delivering a continuously proportioned dose of oxygen and the second gas to the patient. Differential pressure switch 150, connected between the two gas sources, acts to assure that both gas supplies are operational and that the displacers 149 and 152 are both filled to essentially the same pressure. A signal from differential pressure switch 150 is transmitted via 165 to control means 163. Means 163 is arranged such that differential pressure switch 150 must be satisfied before activator 147 may be triggered. This feature ensures that both gases will be delivered in the proper ratio. After a short period, typically about ½ second but long enough for displacers 149 and 152 to empty their contents into cannula 161, the time delay relay in control means 163 deactivates means 147 causing valve 146 to return to its normal position. Gas sources 140 and 141 are re-connected to displacers 152 and 149 respectively, recharging those displacers in preparation for the next triggering signal from the onset of the patient's next inhalation. The cycle then repeats so long as the gases are being administered to the patient.

Although the device of claim 9 has been described as utilizing piston-type displacers such as is illustrated in FIG. 3, displacers of other types as described in the specification could be used as well. For example, piston-type displacers 149 and 152 could be directly replaced by bellows. The displacers of FIG. 9 could also comprise adjustable volume metering chambers of the type illustrated and described in relation to FIG. 4. In this latter embodiment, each of the metering chambers would be pressurized with the gases being administered and blown down into the cannula for dose delivery. This embodiment does eliminate the need for moving the pistons for each expulsion, or dose delivery, but it makes adjustment of the ratio of one gas to the other considerably more difficult and does not assure proper proportioning of the two gases continuously during expulsion as does the apparatus of FIG. 9.

The device of FIG. 9 finds particular use in the administration of anesthetic and/or analgestic gases in the course of surgical procedures, especially in dentistry. Prior art devices used for this purpose typically employ a system for mixing oxygen with another gas, usually nitrous oxide, and require two independent and continuous flow systems, one for each gas. The ratio of oxygen and nitrous oxide is varied during the procedure to achieve the desired sedation effect. It is of critical importance that an adequate level of oxygen be supplied to the patient at every breath and that the nitrous oxide, or other second gas, be supplied only in admixture with oxygen else harm to the patient may well result. The safety factors inherent in the design of the apparatus of FIG. 9, particularly the coupling of the two displacers through a pivoted coordinating lever 154 and the differential pressure switch 150 (which must be satisfied before a dose of gases can be delivered by valve 146 and which may be arranged to activate an alarm as well) effectively preclude the accidental delivery of a single gas to the patient.

Additional advantages provided by this invention over the conventional prior art gas administration devices include the providing of a gas dose to the patient only in response to the onset of an inhalation. This ensures that the major portion of each dose is supplied during the early stages of inhalation; the time when it is most effectively utilized by the patient. By metering each dose and administering it in synchronization with the patient's respiratory cycle, wastage of relatively expensive medical gases is held to a minimum and the buildup of physiologically active gases such as nitrous oxide in the enviornment around the patient is avoided.

In each and all of the embodiments of this invention, the cannula, or other gas delivery means to the patient, is never in direct communication with the source of the respirating gas. Prior art devices can be generally characterized is providing direct communication, or an open flow path, between the source of the respirating gas and the patient while gas delivery is in progress. Pre-metering and temporarily storing each unit dose of respirating gas, as the devices of this invention do, inherently provides safety features nor present in conventional gas delivery systems.

As has been described in relation to the various embodiments, this invention provides both an improved and a simplified way to dispense gases to a patient by effecting a known displacement. The duration of delivery can still be relatively short so as to improve the patient's utilization of the dose but the duration of delivery does not need to be precisely controlled. In fact, by using the method and apparatus of this invention, the time of delivery will tend to be non-linear with variations in prescribed dosages.

Other embodiments of and uses for this invention will be apparatnet to those skilled in the art without departing from the spirit and scope of the following claims.

I claim:

1. A device for supplying premeasured doses of respirating gas to a patient in synchronization with the respiratory cycle of said patient, comprising:
a source of respirating gas at relatively high pressure;
means comprising a cylinder closed at both ends and having disposed within the cylinder a piston member shorter than said cylinder and free to reciprocate back and forth from one end of said cylinder to the other for premetering a single dose quantity of said respirating gas and for temporarily storing said metered dose;

means for sensing the onset of inhalations of said patient and for producing signals in response to said sensing;

gas flow routing means operating independently of the position of said piston member and acting only in response to a sensed inhalation signal for routing the flow of respirating gas back and forth from a first path to a second path in response to said produced signals, said routing means arranged to cause said respirating gas to flow along said first path in response to a produced signal, at a pressure greater than atmospheric, to one interior end of said cylinder and to drive said piston to the other end of said cylinder, said routing means further arranged to cause said respirating gas to flow along said second path in response to a successive produced signal, at a pressure greater than atmospheric, to the other interior end of said cylinder and to drive said piston back to the opposite cylinder end, the movement of said piston from one end of said cylinder to the other serving to drive a metered dose of respirating gas out of said cylinder, and cannula means for conveying said metered dose of respirating gas to the patient, said cannula means arranged to communicate through said flow routing means between the interior end of said cylinder opposite to that of the entering respirating gas and said patient.

2. The device of claim 1 wherein said means for sensing an inhalation comprises a pressure sensor adapted to produce a signal representative of the onset of an inhalation by said patient.

3. The device of claim 2 wherein said gas flow routing means include multi-ported valve means movable between two positions, the first of said valve positions establishing fluid communication between a source of respirating gas at regulated elevated pressure and the interior of said cylinder at a first end thereof and also establishing fluid communication between the interior of said cylinder at the second end thereof and cannula means adapted to convey doses of respirating gas to said patient; the other of said valve positions establishing fluid communication between said source of respirating gas and the interior of said cylinder at the second end thereof and also establishing fluid communication between the interior of said cylinder at the first end thereof and said cannula means.

4. The device of claim 3 including means responding to signals from said sensor causing said valve means to move alternately from one position to the other position.

5. The device of claim 4 wherein said signals are transmitted to a flip-flop relay having a power supply associated therewith; wherein said valve means are solenoid operated, and wherein successive transmitted signals cause said relay and said solenoid to move said valve means from one of said positions to the other of said positions.

6. The device of claim 1 wherein said cylinder has at least one removable end and wherein said piston and cylinder are sized one relative to the other so that the free space within said cylinder with the piston present is proportional to that single dose quantity of respirating gas administered to said patient at each breath.

7. The device of claim 6 wherein said free space within said cylinder is adjustable in volume to thereby allow change of the unit dose of respirating gas administered per breath.

8. The device of claim 2 wherein said cannula means are adapted to discharge said gas into the nasal cavity of said patient, wherein said sensor is in fluid communication with the nasal cavity of said patient through said cannula means, and wherein said sensor is adapted to respond to slight negative pressure changes indicative of the onset of inhalation.

9. The device of claim 8 wherein a line connects said sensor to said cannula means, said line including closure means adapted to isolate said sensor from the cannula for a brief interval after each said signal produced by the sensor thereby shielding said sensor from the blast of respirating gas displaced from said cylinder upon movement of said valve means from one position to the other.

10. The device of claim 9 wherein said closure means comprise a solenoid operated, on-off valve and wherein each said signal transmitted to said relay is transmitted as well to an interval timer which activates said on-off valve.

11. The device of claim 10 wherein said interval is in the range of about ⅜ about ¾ second in length.

12. A method for administering precisely premeasured doses of respirating gas to a patient in synchronization with the respiratory cycle of said patient comprising the following steps:

(a) sensing the onset of an inhalation and producing a signal in response to said sensing;

(b) transmitting said signal to operating means adapted to route the flow of said respirating gas back and forth from a first path to a second path in response to said produced signals;

(c) causing said respirating gas to flow along said first path at a pressure greater than atmospheric to one interior end of a cylinder having a piston disposed therein, the piston being shorter than the length of the cylinder and free to reciprocate from the one cylinder end to the other;

(d) continuing the gas flow along the first path until the piston reaches the other end of the cylinder end the gas pressure within the cylinder behind the piston is substantially equal to the source pressure, the movement of said piston driving gas in front of it out of the cylinder and through conduit means communicating openly with the nasal cavity of said patient;

(e) transmitting another signal representative of the onset of another inhalation of said patient to the operating means thereby causing the flow of said respirating gas to be routed along said second path to the interior of the other cylinder end;

(f) continuing the gas flow along said second path until the piston reaches the one end of the cylinder and the gas pressure within the cylinder behind the piston is substantially equal to the source pressure, the movement of said piston driving gas in front of it out of the cylinder and through said conduit means which communicates directly with the nasal cavity of said patient; and (g) continuing said steps (a) to (f) in response to continued sensed inhalations and produced signals.

* * * * *